US012774975B2

(12) United States Patent
Cao et al.

(10) Patent No.: US 12,774,975 B2
(45) Date of Patent: Oct. 27, 2026

(54) NON-INVASIVE TIME DOMAIN REFLECTION PROBE CALIBRATION METHOD AND SYSTEM

(71) Applicants: China Jikan Research Institute Of Engineering Investigations And Design, Co., Ltd, Xi'an (CN); Xi'an Jiaotong University, Xi'an (CN)

(72) Inventors: Jie Cao, Xi'an (CN); Long Wang, Xi'an (CN); Jiwen Zhang, Xi'an (CN); Zaixin Wan, Xi'an (CN); Qingyi Mu, Xi'an (CN); Dongjing Wang, Xi'an (CN); Yuanqiang Zhou, Xi'an (CN); Zhi Liu, Xi'an (CN); Long Zhang, Xi'an (CN); Hui Li, Xi'an (CN); Jian Chen, Xi'an (CN); Teng Yang, Xi'an (CN); Lei Ran, Xi'an (CN); Jiao Lin, Xi'an (CN); Xiao Dong, Xi'an (CN); Shuai Liu, Xi'an (CN); Weiwei Zhao, Xi'an (CN)

(73) Assignees: China Jikan Research Institute Of Engineering Investigations And Design, Co., Ltd, Xi'an (CN); Xi'an Jiaotong University, Xi'an (CN)

( * ) Notice: Subject to any disclaimer, the term of this patent is extended or adjusted under 35 U.S.C. 154(b) by 461 days.

(21) Appl. No.: 18/360,912

(22) Filed: Jul. 28, 2023

(65) Prior Publication Data

US 2024/0102955 A1 Mar. 28, 2024

(30) Foreign Application Priority Data

Sep. 19, 2022 (CN) ......................... 202211137344.8

(51) Int. Cl.
*G01N 27/04* (2006.01)
*G01N 33/24* (2006.01)

(52) U.S. Cl.
CPC ........... *G01N 27/048* (2013.01); *G01N 33/24* (2013.01)

(58) Field of Classification Search
CPC .... G01N 27/048; G01N 27/221; G01N 33/24; G01N 27/223
See application file for complete search history.

(56) References Cited

U.S. PATENT DOCUMENTS 5,801,537 A * 9/1998 Siddiqui ................ G01R 27/26 324/354
8,947,102 B1 * 2/2015 Evett .................... G01N 27/223 324/634

(Continued)

*Primary Examiner* — Eman A Alkafawi
*Assistant Examiner* — Suresh K Rajaputra
(74) *Attorney, Agent, or Firm* — Sang Young Han

(57) ABSTRACT

A non-invasive time domain reflection probe calibration method includes: using different volume ratio of ethanol and deionized water mixed solution to calculate a test target's medium weight coefficient and waveguide length of the non-invasive time domain reflection probes; using different concentrations of NaCl solutions to calibrate a waveguide geometric dimensioning of the non-invasive time domain reflection probes; preparing compacted soil samples with known different moisture contents and densities, and calibrating a correlation parameter of compacted soil samples' dielectric constant and conductivity with moisture content and density. The method not only determines the sensitivity of the test target medium of the non-invasive time domain reflection probes, but also obtains the waveguide length and geometric dimensioning of the probe, and realizes an accurate test of moisture content and density of the soil. The calibration method has an accurate calibration result, a wide application range, a convenient operation and a strong practicability.

2 Claims, 4 Drawing Sheets

(56) References Cited

U.S. PATENT DOCUMENTS

| | | | | |
|---|---|---|---|---|
| 9,970,969 | B1 * | 5/2018 | Farrington | G01N 33/246 |
| 2004/0201385 | A1 * | 10/2004 | Drnevich | G01N 33/246<br>324/643 |
| 2005/0210995 | A1 * | 9/2005 | Drnevich | G01N 33/383<br>73/803 |
| 2013/0110398 | A1 * | 5/2013 | Drnevich | G01N 33/246<br>702/2 |

* cited by examiner

NON-INVASIVE TIME DOMAIN REFLECTION PROBE CALIBRATION METHOD AND SYSTEM

CROSS REFERENCE TO THE RELATED APPLICATIONS

This application is based upon and claims priority to Chinese Patent Application No. 202211137344.8, filed on Sep. 19, 2022, the entire contents of which are incorporated herein by reference.

TECHNICAL FIELD

The present invention belongs to the field of geotechnical engineering measuring instrument calibration technology, and particularly relates to a non-invasive time domain reflection probe calibration method and system.

BACKGROUND

As a technology that can simultaneously measure the soil moisture content and density, time domain reflection technology is widely used in geotechnical engineering, soil science and other disciplines. With the promotion of engineering applications, as an important part of time domain reflection technology, the time domain reflection probes have developed rapidly. According to testing mold, the time domain reflection probes can be divided into invasive probes and non-invasive probes. For invasive probes, they can be divided into a fixed-point type and a penetrating type according to the design form and test purpose. Fixed-point probes (such as coaxial type, two-needle type, two-plate type and three-needle type, etc.) can only be embedded in the surface layer of the soil to test the soil moisture content and density at fixed point position; the penetration probes can continuously test the soil moisture content and density at different depths. The invasive probes need to be inserted into the soil during the test, resulting in the extrusion of the soil to be tested ('squeezing effect'), thereby generating test errors. For non-invasive probes (such as circuit board type), because they do not need to be inserted into the soil during the test process, the problem of 'squeezing effect' of the invasive probes is overcome. However, for non-invasive time-domain reflection probes, the calibration procedure before testing is the premise to ensure the reliability of test results of soil moisture content and density.

At present, it is known that the calibration procedure for testing soil moisture content and density by time domain reflection technology is mainly aimed at invasive probes. The calibration procedure mainly includes: the calibration of the waveguide length and geometric dimensioning of the probes, calibration of correlation parameters of soil dielectric constant and conductivity with water rate and density. For the calibration of the soil moisture content and density tested by the invasive probes, firstly, using deionized water to calibrate waveguide length of the probes; then using different concentrations of NaCl solution to calibrate waveguide geometric dimensioning of the probes; finally, using compacted soil samples of known different moisture contents and densities to calibrate correlation parameters of soil dielectric constant and conductivity with water rate and density. Although the calibration procedure is simple and mature, it is not suitable for non-invasive time domain reflection probes. This is mainly due to the fact that the non-invasive time domain reflection probes attach waveguide to circuit board substrate, the above design method avoids insertion of the probes into the soil during the test, meanwhile, it also results in the probes containing both the target soil and the circuit board substrate. Therefore, to accurately test the soil moisture content and density, it is necessary to scientifically design a calibration procedure to eliminate the influence of the circuit board substrate in invasive time domain reflection probes on the test results.

In summary, the existing calibration procedure for testing soil moisture content and density by invasive time domain reflection probes is relatively mature, but it is not suitable for non-invasive time domain reflection probes.

SUMMARY

The technical problem to be solved by the present invention lies in the deficiency of the above existing technology, and the present invention provides a non-invasive time domain reflection probe calibration method and system, which is used to solve the technical problem that the non-invasive time domain reflection probes cannot accurately test the calibration of the soil moisture content and density.

The present invention adopts the following technical scheme:

a non-invasive time domain reflection probe calibration method, using different volume ratio of ethanol and deionized water mixed solution to calculate a test target's medium weight coefficient and waveguide length of the non-invasive time domain reflection probes; based on the test target's medium weight coefficient, using different concentrations of NaCl solution to calibrate waveguide geometric dimensioning of the non-invasive time domain reflection probes; preparation of compacted soil samples with known different moisture contents and densities, according to the waveguide length and waveguide geometric dimensioning of non-invasive time domain reflection probes, calibrating a correlation parameter of compacted soil samples' dielectric constant and conductivity with moisture content and density.

Specifically, step S1 is specified as:

S101. mixing ethanol and deionised water to form at least 4 groups of mixed solution with different concentrations, then using the invasive time domain reflection probes and non-invasive time domain reflection probes to test respectively the time domain reflection waveform graphs of mixed solutions with different concentrations, finally calculating a dielectric constant of the mixed solutions according to the time domain reflection waveform graphs of invasive time domain reflection probes test, and obtaining a propagation time of electromagnetic wave along the waveguide $\Delta t_e$ from the time domain reflection waveform graphs tested by the invasive time domain reflection probes;

S102. according to the dielectric mixed model, the regression analysis is used to study an effective dielectric constant tested by non-invasive time domain reflection probes, the dielectric constant of mixed solutions tested by invasive time domain reflection probes test and a dielectric constant tested by circuit board substrate medium, calculating and obtaining a test target's medium weight coefficient and a waveguide length tested by the non-invasive time domain reflection probes.

Further, in step S102, the test target's medium weight coefficient m and waveguide length $L_e$ of the non-invasive time domain reflection probes are:

$$m = \frac{a}{4L_e^2}$$

-continued $$L_e = \sqrt{\frac{aK_m + b}{4K_m}}$$

wherein, $K_m$ is the dielectric constant of circuit board substrate medium, a and b are fitting parameters of dielectric mixed model regression analysis formula.

Specifically, step S2 is specified as:

S201. considering the reasonable conductivity gradient and configuring more than or equal to four groups different concentrations of NaCl solutions, then using invasive time domain reflection probes and non-invasive time domain reflection probes to test time domain reflection waveform graphs of NaCl solutions at a constant temperature, calculating a conductivity of NaCl solution according to the time domain reflection waveform graphs tested by invasive time domain reflection probes, and obtaining an initial voltage of the electromagnetic pulse $V_{e0}$ and a stable voltage after multiple reflections $V_{e\infty}$ from time domain reflection waveform graphs tested by non-invasive time domain reflection probes;

S202. according to a conductivity mixed model, a regression analysis is used to study an effective conductivity tested by non-invasive time domain reflection probes, a conductivity tested by invasive time domain reflection probes and a conductivity of circuit board substrate medium, calculating and obtaining a waveguide geometric dimensioning $C_e$ of the non-invasive time domain reflection probes.

Further, in step S201, the conductivity of NaCl solution tested by the invasive time domain reflection probes is:

$$EC_s = \frac{1}{C}\left(\frac{2V_0 - V_\infty}{V_\infty}\right)$$

wherein, C is the waveguide geometric dimensioning of the invasive time domain reflection probes, and $V_0$ is the initial voltage of the electromagnetic pulse tested by invasive time domain reflection probes, and $V_\infty$ is the stable voltage after multiple reflections tested by the invasive time domain reflection probes.

Further, in step S202, the waveguide geometric dimensioning $C_e$ of the non-invasive time domain reflection probes is:

$$C_e = \frac{2V_{e0} - V_{e\infty}}{V_{e\infty} EC_s}$$

wherein, $EC_s$ is the conductivity of NaCl solution tested by the invasive time domain reflection probes.

Specifically, step S3 is specified as:

S301. configuring the dried and sieved soil as compacted soil samples covering the range of tested moisture content, and the number of compacted soil samples is greater than or equal to 4 groups, then combining with the waveguide length and waveguide geometric dimensioning of the non-invasive time domain reflection probes, using the non-invasive time domain reflection probes to test time domain reflection waveform graphs of compacted soil samples, and using dielectric and conductivity mixed model to calculate a dielectric constant $K_s$ and a conductivity $EC_s$ of compacted soil samples respectively;

S302. using the formula to make a regression analysis of the dielectric constant $K_s$ and the conductivity $EC_s$ of the soil obtained by a dielectric and conductivity mixed model, obtaining calibration parameters $a_1$, $b_1$, $c_1$ and $d_1$.

Further, in step S301, the dielectric constant $K_s$ and conductivity $EC_s$ of compacted soil samples are respectively:

$$K_s = \frac{K_e + (m-1)K_m}{m}$$

$$EC_s = \frac{2V_{e0} - V_{e\infty}}{C_e V_{e\infty}}$$

wherein, $K_e$ is an effective dielectric constant tested by the non-invasive time domain reflection probes, m is a test target's medium weight coefficient of the non-invasive time domain reflection probes, $K_m$ is a dielectric constant of the circuit board substrate medium, $V_{e0}$ is an initial voltage of the electromagnetic pulse tested by the non-invasive time domain reflection probes, $V_{e\infty}$ is a stable voltage after multiple reflections tested by the non-invasive time domain reflection probes, $C_e$ is a waveguide geometric dimensioning of the non-invasive time domain reflection probes.

Further, in step S302, a volumetric moisture content θ and a soil density $\rho_c$ of compacted soil samples are calculated as follows:

$$\theta = a_1\sqrt{K_s} + b_1$$

$$\frac{EC_s}{\rho_c} = c_1 K_s + d_1.$$

Secondly, the example of the present invention provides a non-invasive time domain reflection probe calibration system, including:

- a calculation module, which is used to calculate test target's medium weight coefficient and waveguide length of the non-invasive time domain reflection probes by using the mixed solutions of ethanol and deionized water with different volume ratios;
- a regression module, which is used to utilize test target's medium weight coefficient obtained by the calculation module, and use different concentrations of NaCl solution to calibrate the waveguide geometric dimensioning of the non-invasive time domain reflection probe;
- a calibration module, which is used to prepare compacted soil samples with known different moisture contents and densities, according to the waveguide length of non-invasive time domain reflection probes obtained by the calibration module and waveguide geometric dimensioning obtained by the regression module, and calibrate correlation parameters of compacted soil samples' soil dielectric constant and conductivity with moisture content and density.

Compared with the existing technology, the present invention has at least the following beneficial effects:

the present invention relates to a non-invasive time domain reflection probe calibration method, using the mixed solutions of ethanol and deionized water with different volume ratios to calibrate the test target's medium weight coefficient and waveguide length of non-invasive time domain reflection probes; based on the test target's medium weight coefficient, using different concentrations of NaCl solutions to calibrate waveguide geometric dimensioning of the non-invasive time domain reflection probes; finally, preparation of compacted soil samples with known different moisture contents and densities, according to the waveguide length and waveguide geometric dimensioning of non-invasive time domain reflection probes, calibrating correlation parameters of compacted soil samples' dielectric constant and conductivity with moisture content and density, and establishingt a link between compacted soil samples' dielectic constant and conductivity with moisture content and density, providing an effective path for laboratory test and field engineering application of non-invasive time domain reflection probes in geotechnical engineering field.

Further, using different volume ratios of ethanol and deionized water mixed solutions, which can not only make the dielectric constant of the solutions used in the test have a certain interval, but also ensure the uniformity of the solutions. Setting a reasonable concentration gradient and configuring more than or equal to 4 groups of solutions, which can ensure that the dielectric constant range of the mixed solutions can contain the dielectric constant of the soil to be tested, and ensure the representativeness of the regression analysis parameters. Adopting time-domain reflection technology to test dielectric constant of ethanol and deionized water mixed solutions and propagation time of electromagnetic wave along the waveguide, the test is accurate, the principle is clear, the technology is mature and the operation is simple. Combined with the effective dielectric constant tested by the non-invasive time domain reflection probes, the dielectric constant of the mixed solutions tested by the invasive time domain reflection probes and the dielectric constant of circuit board substrate medium, using the dielectric mixed model to make regression analysis, calculating and obtain the test target's medium weight coefficient m and waveguide length $L_e$ of the non-invasive time domain reflection probes, according to the characteristics of non-uniform distribution of potential field energy around the waveguide of non-invasive time domain reflection probes, using weight allocation theory to make a quantitative solution aiming at the energy weight coefficient of potential field in different regions around the waveguide, and obtaining test target's medium weight coefficient m and the waveguide length $L_e$.

Further, obtaining the test target's medium weight coefficient m of the non-invasive time domain reflection probes, which can determine and preclude the effects of the circuit board substrate medium when it is used to test the soil dielectric constant/conductivity with non-invasive time domain reflection probes; obtaining the waveguide length $L_e$ of the non-invasive time domain reflection probes, which can preclude the influence of fabrication errors on waveguide length, thereby ensuring the accuracy of the test results.

Further, considering the reasonable conductivity gradient and configuring more than or equal to 4 groups of NaCl solutions with different concentrations, which can ensure that the conductivity range of the mixed solutions can include the conductivity of the soil to be tested, and ensure the representativeness of the regression analysis parameters. Adopting time-domain reflection technology to test conductivity of NaCl solutions, initial voltage $V_{e0}$ of the electromagnetic pulse, stable voltage $V_{e\infty}$ after multiple reflections, the test is accurate, the principle is clear, the technology is mature and the operation is simple. Combined with the effective conductivity tested by the non-invasive time domain reflection probes, the conductivity of the mixed solutions tested by the invasive time domain reflection probes and the conductivity of circuit board substrate medium, using the conductivity mixed model to make regression analysis, obtaining the waveguide geometric dimensioning $C_e$ of non-invasive time domain reflection probes, according to the characteristics of non-uniform distribution of potential field energy around the waveguide of non-invasive time domain reflection probes, using weight allocation theory to make a quantitative solution aiming at the energy weight coefficient of potential field in different regions around the waveguide, and obtaining the waveguide geometric dimensioning $C_e$.

Further, using invasive time domain reflection probes to test the conductivity $EC_s$ of NaCl solution, the test is accurate, the principle is clear, the technology is mature and the operation is simple, it can provide accurate conductivity values of different concentrations of NaCl solutions and provide parameters for regression analysis of conductivity mixed model.

Further, determining the waveguide geometric dimensioning $C_e$ of the non-invasive time domain reflection probes, which can determine comprehensive influence value of the geometric and physical properties of transmission lines and waveguide arrangement of non-invasive time domain reflection probes on the conductivity calculation of target medium, improving the accuracy of the conductivity test results by non-invasive time domain reflection probes.

Further, configuring the dried and sieved soil samples as compacted soil samples s covering the test moisture content range and greater than or equal to 4 groups, this procedure not only standardizes the preparation steps of compacted samples, but also provides support for the representativeness of subsequent dielectric constant and conductivity calibration parameters. Using non-invasive time domain reflection probe parameters calibrated and calculated, testing and calculating the dielectric constant $K_s$ and conductivity $EC_s$ of compacted soil samples, the technology is mature and the theory is reliable, meanwhile considering the effects of probe parameters and temperature on the dielectric constant and conductivity of soil samples, improving the accuracy and repeatability of the test results. Using calculation formula to calibrate dielectric constant and conductivity, establishing the relationship between dielectric constant and conductivity and soil density and volumetric moisture content, providing calibration values that possesses representative parameters $a_1$, $b_1$, $c_1$ and $d_1$ in the laboratory calibration tests of non-invasive time domain reflection probes.

Further, by testing and calculating the dielectric constant and conductivity of the compacted soil samples with non-invasive time-domain reflection probes, the theoretical model is used to preclude the influence of the dielectric properties of the circuit board substrate and the parameter error of the probe/transmission line itself on the dielectric properties of the target medium to be tested, achieving accurate calculation of dielectric constant and conductivity of compacted soil samples, providing a theoretical basis for the non-invasive time domain reflection probes to accurately test the dielectric properties of compacted soil samples.

Further, by combining the dielectric constant and conductivity of the compacted soil samples tested by non-invasive time domain reflection probes with calibrated parameters $a_1$, $b_1$, $c_1$ and $d_1$, calculating the moisture content and density of soil samples, establishing a link between dielectric constant and conductivity of compacted soil samples and density and moisture content, providing theoretical support for laboratory test and engineering application of non-invasive time domain reflection probes in geotechnical engineering.

Understandably, the beneficial effects of the above second aspects can be seen in the relevant descriptions in the above first aspects, which will not be repeated here.

In summary, the present invention can determine the sensitivity of the test target medium of the non-invasive time domain reflection probes, and realize accurate calibration of the probe parameters, establishing a link between dielectric constant and conductivity of compacted soil samples and density and moisture content. The method and system theory are clear, the calibration results are accurate, the application range is wide, the technology is reliable, the operation is convenient and the practicability is strong.

The following is a further detailed description of the technical scheme of the invention through the drawings and embodiments

BRIEF DESCRIPTION OF THE DRAWINGS

FIGS. 1A-1C are equipment diagrams of non-invasive time domain reflection of the present invention, wherein, FIG. 1A is a calibration chart of non-invasive time domain reflection device; FIG. 1B is an outline drawing of non-invasive time domain reflection probes; FIG. 1C is a plane arrangement chart of non-invasive time domain reflection probes;

FIGS. 4A and 4B show correlation parameter calibration results that soil dielectric constant and conductivity and moisture content and density of non-invasive time domain reflection probes of the present invention, wherein, FIG. 4A shows moisture content, and FIG. 4B shows density.

Figure 1A:
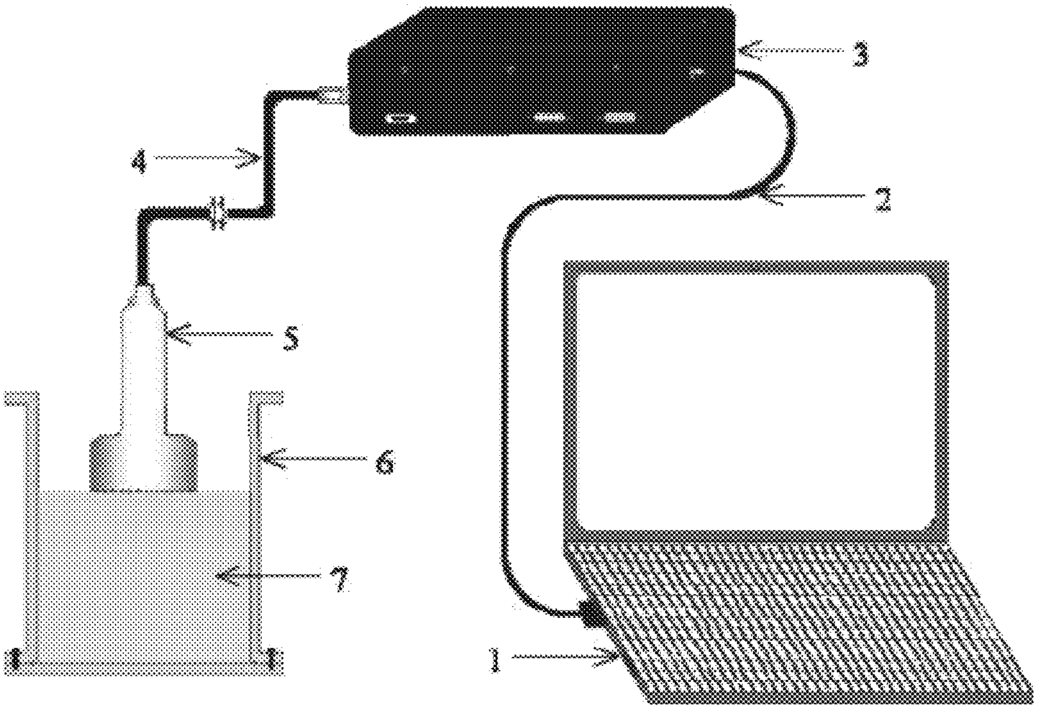

Wherein, 1. computer; 2. data line; 3. time domain signal processor; 41. coaxial cable; 5. non-invasive time domain reflection probe; 6. acrylic bucket; 7. target test medium; 8. epoxy resin; 9. circuit board; 10. waveguide.

DETAILED DESCRIPTION OF THE EMBODIMENTS

In the following, the technical scheme in the embodiment of the present invention will be clarified and completed in combination with the attached diagram of the embodiment of the present invention. Obviously, the embodiment described is part of the embodiment of the present invention, not the whole embodiment. Based on the embodiments in the present invention, all other embodiments obtained by ordinary technicians in this field without making creative labor belong to the scope of protection of the present invention.

In the description of the present invention, it is to be understood that the terms "including" and "comprising" indicate the presence of the described feature, whole, step, operation, element and/or component, but do not exclude the presence or addition of one or more other features, whole, steps, operations, elements, components and/or collections thereof.

It should also be understood that the terminology used in the specification of the invention is for the purpose of describing particular embodiments only and is not intended to limit the invention. As used in the specification of the invention and the appended claims, the singular forms "one", "a" and "the", unless the context clearly indicates otherwise, are intended to include the plural forms.

It should also be further understood that the term 'and/or' used in the specification of the present invention and the accompanying claims refers to any combination of one or more of the associated listed items and all possible combinations, and includes these combinations, for example, A and/or B, which may be expressed in three cases: A alone, A and B together, and B alone. In addition, the character '/' in this article generally indicates that the object is an 'or' relationship.

It should be understood that, although terms first, second, third, etc. may be used in embodiments of the present invention to describe preset ranges, etc., these preset ranges should not be limited to these terms. These terms are only used to distinguish preset ranges from each other. For example, without deviating from the scope of the embodiment of the invention, the first preset range can also be called the second preset range, similarly, the second preset range can also be called the first preset range.

Depending on the context, e.g. the word "if" used here could be interpreted as "at . . . " or "when . . . " or "in response to a determination" or "in response to a detection". Similarly, depending on the context, the phrase "if determined" or "if detected (the stated condition or event)" may be interpreted as "when determined" or "in response to a determination" or "when detecting (a stated condition or event)" or "in response to detecting (a stated condition or event)".

In the attached diagram, various structural schematic diagrams of the public embodiment according to the invention are shown. These figures are not drawn in proportion, in which some details are enlarged for the purpose of clear expression, and some details may be omitted. The shapes of various regions and layers shown in the figure and the relative size and positional relationship between them are only illustrative. In practice, there may be deviations due to manufacturing tolerances or technical limitations, and technicians in this field can design additional regions/layers with different shapes, sizes, and relative positions according to actual needs.

The present invention provides a non-invasive time domain reflection probe calibration method, using different volume ratio of ethanol and deionized water mixed solution to calculate the test target's medium weight coefficient and waveguide length of the non-invasive time domain reflection probes; using different concentrations of NaCl solution to calibrate waveguide geometric dimensioning of the non-invasive time domain reflection probes; preparation of compacted soil samples with known different moisture contents and densities, calibrating correlation parameters of the tested soil dielectric constant and conductivity with moisture content and density. The method of the invention can not only determine the sensitivity of the test target's medium of the non-invasive time domain reflection probes, the step theory is clear, the calibration result is accurate, the application range is wide, the technology is reliable, the operation is convenient, and the practicability is strong. It can become a new means in the field of geotechnical engineering measuring instrument calibration technology.

Figure 1B:
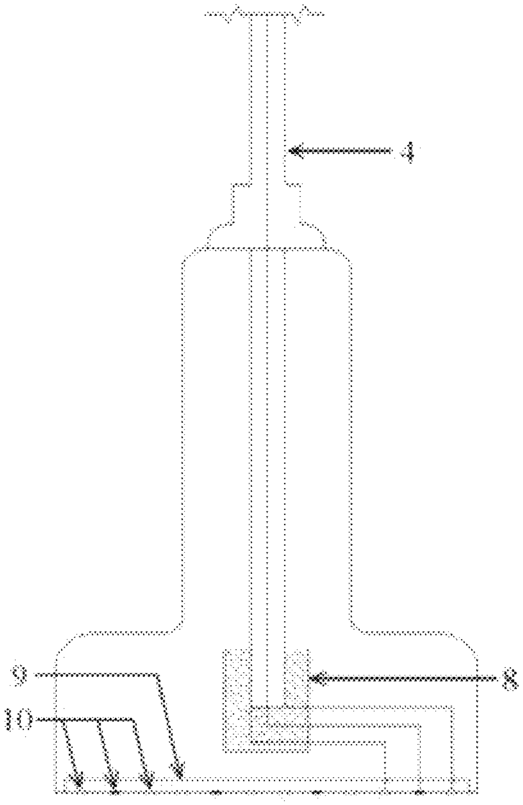
Figure 1C:
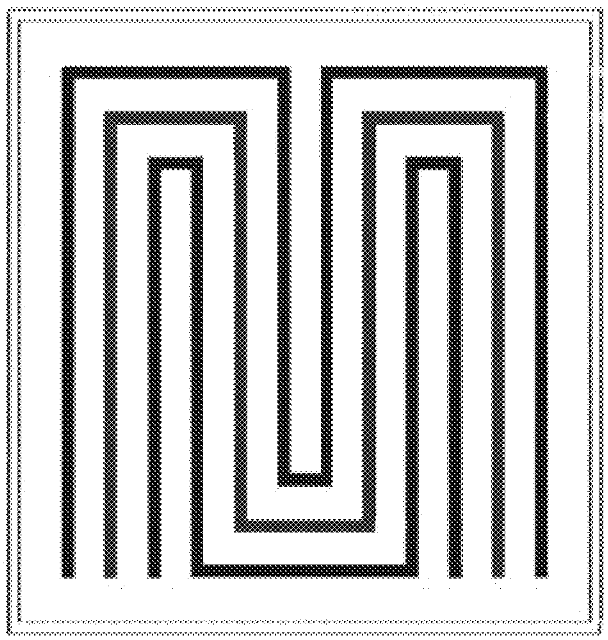

Please see FIGS. 1A-1C, a non-invasive time domain reflection equipment includes computer 1, data line 2, time domain signal processor 3, coaxial cable 4, non-invasive time domain reflection probe 5, acrylic bucket 6 and target test medium 7; the non-invasive time domain reflection probe 5 includes epoxy resin 8, circuit board 9 and waveguide 10.

The portable computer 1 is connected by data line 2 and time domain signal processor 3, and then the time domain signal processor 3 is connected by the coaxial cable 4 and the waveguide 10 of the non-invasive time domain reflection probe 5, finally, the waveguide 10 is attached to the circuit board 9 and is closely attached to the target test medium 7.

In addition, the end of coaxial cable 4 is equipped with epoxy resin 8, and the waveguide 10 is a three-plate type, adopting the gold guide with a width of 1.5 mm and a thickness of 0.03 mm, and the center distance between two gold guides is 4 mm.

A non-invasive method of calibrating a time domain reflection probe of the present invention, comprising the steps:

S1. using the invasive time domain reflection probes and non-invasive time domain reflection probes to test respectively the time domain reflection waveform graphs of different volume ratio of ethanol and deionized water mixed solutions (greater than or equal to 4 groups), then calculating the dielectric constant of the mixed solution according to the time domain reflection waveform graphs, finally the regression analysis of the dielectric constant/effective dielectric constant tested by invasive/non-invasive time domain reflection probes and the dielectric constant of the circuit board substrate medium is carried out by using the dielectric mixed model, calculating and obtaining the test target's medium weight coefficient and waveguide length tested by the non-invasive time domain reflection probes;

using the invasive time domain reflection probes and non-invasive time domain reflection probes to test respectively the time domain reflection waveform graphs of different volume ratio of ethanol and deionized water mixed solutions (greater than or equal to 4 groups), then calculating the dielectric constant of the mixed solution according to the time domain reflection waveform graphs, finally the regression analysis of the dielectric constant/effective dielectric constant tested by invasive/non-invasive time domain reflection probes and the dielectric constant of the circuit board substrate medium is carried out by using the dielectric mixed model, calculating and obtaining the test target's medium weight coefficient and waveguide length tested by the non-invasive time domain reflection probes, which is specifically as follow:

S101. using different volume ratios of ethanol and deionized water mixed solutions, setting a reasonable concentration gradient and configuring more than or equal to 4 groups of mixed solutions, then using the invasive time domain reflection probes and non-invasive time domain reflection probes to test respectively the time domain reflection waveform graphs of mixed solutions with different concentrations, finally calculating the dielectric constants of the mixed solutions according to the time domain reflection waveform graphs of invasive time domain reflection probes test, and obtaining a propagation time of electromagnetic wave along the waveguide $\Delta t_e$ from the time domain reflection waveform graphs of invasive time domain reflection probes test.

The calculation formula of the mixed solutions' dielectric constant tested by the invasive time domain reflection probes is as follows:

$$K_s = \frac{(c\Delta t)^2}{4L^2} \tag{1}$$

wherein $K_s$ is the mixed solutions' dielectric constant tested by the invasive time domain reflection probes, c is the propagation velocity of the electromagnetic wave in vacuum ($3\times10^8$ m/s), $\Delta t$ is the propagation time of the electromagnetic wave along the waveguide tested by the invasive time-domain reflection probes, and L is the waveguide length of the invasive time-domain reflection probes.

S102. According to the dielectric mixed model, the regression analysis is used to study effective dielectric constant's expression formula tested by non-invasive time domain reflection probes, dielectric constant of mixed solutions tested by invasive time domain reflection probes test and dielectric constant of circuit board substrate medium, and the test target's medium weight coefficient and waveguide length tested by the non-invasive time domain reflection probes are calculated and obtained.

The waveguide length calculation formula of the dielectric mixed model and the non-invasive time domain reflection probes is as follows:

$$K_e^n = mK_s^n + (1-m)K_m^n \tag{2}$$

$$L_e = \sqrt{\frac{aK_m + b}{4K_m}} \tag{3}$$

Wherein, $K_e$ is the effective dielectric constant tested by the non-invasive time domain reflection probes, $K_m$ is the dielectric constant of circuit board substrate medium, m is the test target's medium weight coefficient of the non-invasive time domain reflection probes, $L_e$ is the waveguide length of the non-invasive time domain reflection probes, a and b are the fitting parameters of regression analysis formula of dielectric mixed model, and n is the shape parameter of the target medium relative to the applied electric field ($-1 \le n \le 1$). When the target medium is combined with the capacitor in parallel, n=1, and when the target medium is combined with the capacitor in perpendicular, n=−1; the present invention uses the target medium combined with the capacitor in parallel, i.e. n=1.

The regression analysis equation of dielectric mixed model and the test target's medium weight coefficient m are calculated as follows:

$$y = aK_s + b \tag{4}$$

$$m = \frac{a}{4L_e^2} \tag{5}$$

the variables and constants in the regression analysis calculation formula of the dielectric mixed model are calculated as follows:

$$y = (c\Delta t_e)^2 \tag{6}$$

$$a = 4mL_e^2 \tag{7}$$

$$b = 4(1-m)L_e^2 K_m \tag{8}$$

Wherein, $\Delta t_e$ is the propagation time of the electromagnetic wave along the waveguide tested by the non-invasive time domain reflection probes.

S2. using the invasive time domain reflection probes and non-invasive time domain reflection probes to test respectively the time domain reflection waveform graphs of different concentrations of NaCl solutions (greater than or equal to 4 groups), then calculating the conductivity of NaCl solutions according to time domain reflection waveform graphs, finally carrying out the regression analysis of the conductivity/effective conductivity tested by invasive/non-invasive time domain reflection probes and the conductivity of the circuit board substrate medium by using the conductivity mixed model, calculating and obtaining the waveguide geometric dimensioning of the probes:

using the invasive time domain reflection probes and non-invasive time domain reflection probes to test respectively the time domain reflection waveform graphs of different concentrations of NaCl solutions (greater than or equal to 4 groups), then calculating the conductivity of NaCl solutions according to time domain reflection waveform graphs, finally carrying out the regression analysis of the conductivity/effective conductivity tested by invasive/non-invasive time domain reflection probes and the conductivity of the circuit board substrate medium by using the conductivity mixed model, calculating and obtaining the waveguide geometric dimensioning of the probes, specifically as follow:

S201. considering the reasonable conductivity gradient and configuring different concentrations of NaCl solutions (more than or equal to 4 groups), then using invasive time domain reflection probes and non-invasive time domain reflection probes to test time domain reflection waveform graphs of NaCl solution at a constant temperature, calculating the conductivity of NaCl solution according to the time domain reflection waveform graphs tested by invasive time domain reflection probes, and obtaining the initial voltage of the electromagnetic pulse $V_{e0}$ and the stable voltage after multiple reflections $V_{e\infty}$ from time domain reflection waveform graphs tested by non-invasive time domain reflection probes;

The conductivity tested by the invasive time domain reflection probes is calculated as follows:

$$EC_s = \frac{1}{C}\left(\frac{2V_0 - V_\infty}{V_\infty}\right) \tag{9}$$

Wherein, $EC_s$ is the conductivity tested by the invasive time domain reflectometry probes, C is the waveguide geometric dimensioning of the invasive time domain reflection probes, and $V_0$ is the initial voltage of the electromagnetic pulse tested by invasive time domain reflection probes, and $V_\infty$ is the stable voltage after multiple reflections tested by the invasive time domain reflection probes.

S202. according to conductivity mixed model, the regression analysis is used to study the expression formula of effective conductivity tested by non-invasive time domain reflection probes test, the conductivity tested by invasive time domain reflection probes and the conductivity of circuit board substrate medium, calculating and obtaining the waveguide geometric dimensioning $C_e$ of the non-invasive time domain reflection probes.

The conductivity mixed model and the waveguide geometric dimensioning $C_e$ of the non-invasive time domain reflection probes are calculated as follows:

$$EC_e^n = mEC_s^n + (1-m)EC_m^n \tag{10}$$

$$C_e = \frac{2V_{e0} - V_{e\infty}}{V_{e\infty}EC_s} \tag{11}$$

Wherein, $EC_e$ is the effective conductivity tested by the non-invasive time domain reflection probes, $EC_m$ is the conductivity of the circuit board substrate medium, $C_e$ is the waveguide geometric dimensioning of the non-invasive time domain reflection probes, $V_{e0}$ is the initial voltage of the electromagnetic pulse tested by non-invasive time domain reflection probes, and $V_\infty$ is the stable voltage after multiple reflections tested by the invasive time domain reflection probes.

The regression analysis of the conductivity mixed model is calculated as follows:

$$y = cEC_s \tag{12}$$

Wherein, c is a fitting parameter of the regression analysis formula of the conductivity mixed model.

The variables and constants in the regression analysis of the conductivity mixed model are as follows:

$$y = \frac{2V_{e0} - V_{e\infty}}{V_{e\infty}} \tag{13}$$

$$c = C_e. \tag{14}$$

S3. using the non-invasive time domain reflection probes to test the time domain reflection waveform graphs of compacted soil samples with different known moisture content and density (greater than or equal to 4), calculating the dielectric constant and conductivity of soil by combining with the waveguide length and geometric dimensioning of the non-invasive time domain reflection probes, then making the regression analysis of dielectric constant and conductivity of the soil and moisture content and density with correlative models, and obtaining the correlation parameters of the dielectric constant and conductivity of the soil with moisture content and density.

Combining with the waveguide length and geometric dimensioning of the non-invasive time domain reflection probes, adopting the time domain reflection waveform graphs obtained from testing the compacted soil samples (greater than or equal to 4 groups) with different moisture content by the non-invasive time domain reflection probes, then making the regression analysis of dielectric constant and conductivity of the soil and moisture content and density with correlative models, and the correlation parameters, specifically as follow:

S301. changing the moisture content by keeping the dry density of the soil constant, configuring the dried and sieved soil as compacted soil samples (greater than or equal to 4 groups) covering the range of tested moisture content, then combining with the waveguide length and waveguide geometric dimensioning of the non-invasive time domain reflection probes, using the non-invasive time domain reflection probes to test the time domain reflection waveform graphs of compacted soil samples, and using dielectric and conductivity mixed model to calculate the dielectric constant ($K_s$) and conductivity ($EC_s$) of compacted soil samples respectively;

the dielectric constant $K_s$ and conductivity $EC_s$ of compacted soil samples are respectively:

$$K_s = \frac{K_e + (m-1)K_m}{m} \tag{15}$$

$$EC_s = \frac{2V_{e0} - V_{e\infty}}{C_eV_{e\infty}} \tag{16}$$

S302. using the formula to make regression analysis of the dielectric constant $K_s$ and conductivity $EC_s$ of the soil obtained by the dielectric and conductivity mixed model, obtaining calibration parameters $a_1$, $b_1$, $c_1$ and $d_1$.

The calibration calculation of moisture content and density of compacted soil samples is as follows:

$$\theta = a_1\sqrt{K_s} + b_1 \quad (17)$$

$$\frac{EC_s}{\rho_c} = c_1 K_s + d_1 \quad (18)$$

Wherein, θ is volumetric moisture content, $a_1$, $b_1$, $c_1$ and $d_1$ are calibration parameters, $\rho_c$ is density of soil sample.

In addition, the effective dielectric constant tested by the non-invasive time domain reflection probes is calculated as:

$$K_e = \frac{(c\Delta t_e)^2}{4L_e^2}. \quad (19)$$

Another embodiment of the present invention, provides a non-invasive time domain reflection probe calibration system, which can be used to realize the above non-invasive time domain reflection probe calibration method, specifically, the non-invasive time domain reflection probe calibration system includes a calculation module, a regression module and a calibration module.

Wherein, the calculation module is used to calculate test target's medium weight coefficient and waveguide length of the non-invasive time domain reflection probes by using the mixed solutions of ethanol and deionized water with different volume ratios;

the regression module is used to utilize test target's medium weight coefficient obtained by the calculation module, and use different concentrations of NaCl solution to calibrate the waveguide geometric dimensioning of the non-invasive time domain reflection probe:

the calibration module is used to prepare compacted soil samples with known different moisture contents and densities, and according to the waveguide length of non-invasive time domain reflection probes obtained by the calibration module and waveguide geometric dimensioning obtained by the regression module, calibrate correlation parameters of compacted soil samples' soil dielectric constant and conductivity with moisture content and density In order to make the purpose, technical scheme and advantages of the embodiment of the present invention more clear, the following will describe the technical scheme of the embodiment of the invention clearly and completely in combination with the attached figure of the embodiment of the invention. Obviously, the described embodiments are some embodiments of the invention but not all embodiments. The components of the embodiment of the present invention, which are usually described and shown in the diagram attached here, can be arranged and designed in various configurations. Therefore, the following detailed description of the embodiment of the invention provided in the drawings is not intended to limit the scope of the invention requiring protection, but merely to indicate the selected embodiment of the present invention.

Embodiment

Non-invasive time domain reflection probes: the waveguide of the non-invasive time domain reflection probe calibrated in the embodiment is three-plate type and uses gold guide plate with the width of 1.5 mm and the thickness of 0.03 m, the average length of the three metal plates is 173 mm, and the center distance between two gold guide plates is 4 mm. In addition, the circuit board substrate of the probes adopts epoxy resin with the conductivity of OS/m and dielectric constant of 3.1.

S1: configuring the mixed solutions of ethanol and deionized water in a gradient of 0%, 20%, 40%, 60%, 80% and 100% by volume of ethanol and deionized water, and testing the time domain reflection waveform graphs of ethanol and deionized water mixed solutions with different volume ratios by invasive and non-invasive time domain reflection probes at a constant temperature conditions, finally, according to the time domain reflection waveform graphs tested by the invasive time domain reflection probes, calculating the dielectric constant of the mixed solutions according to formula (1), and obtaining the propagation time $\Delta t_e$ of electromagnetic wave along the waveguide from the time domain reflection waveform graphs tested by the non-invasive time domain reflection probes. Further, using the dielectric mixed model formula (2) and combining the expression formula of effective dielectric constant tested by the non-invasive time domain reflection probe, the dielectric constant and dielectric constant of circuit board substrate medium tested by the invasive time domain reflection probes, according to the dielectric mixed model, making the regression analysis on formula (4), finally, calculating and obtaining the test target's medium weight coefficient m and waveguide length $L_e$ of the non-invasive time domain reflection probes, 0.47 and 175 mm respectively.

Figure 2:
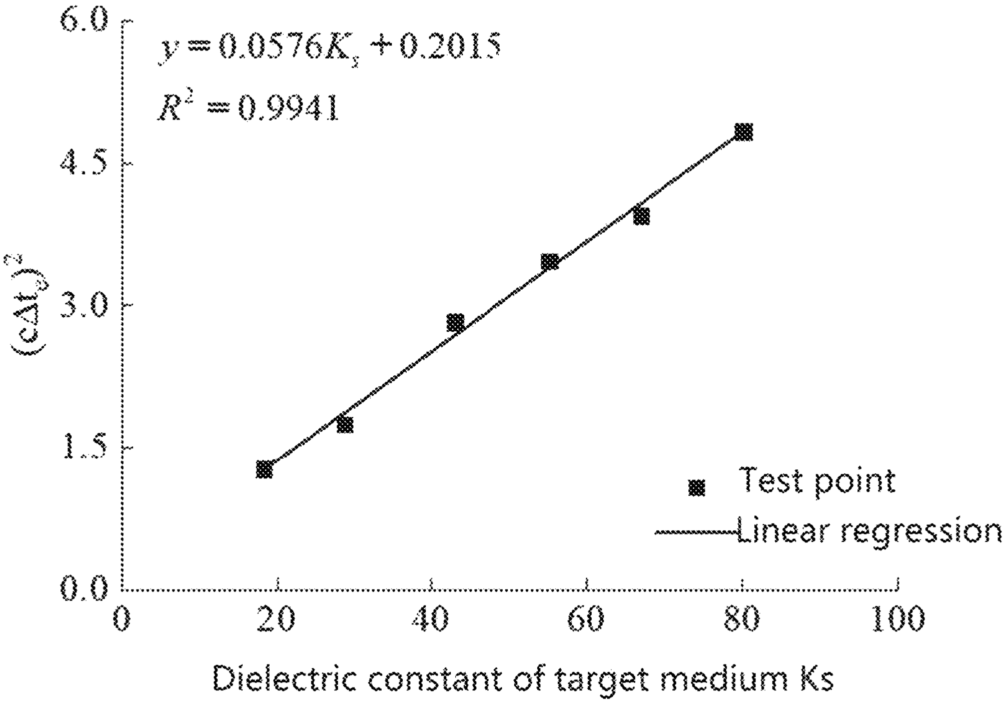
FIG. 2 is a analysis result map of the test target's medium weight coefficient of the present invention.

Specifically, the analysis results of the test target's medium weight coefficient of the non-invasive time domain reflection probes are shown in FIG. 2.

Figure 3:
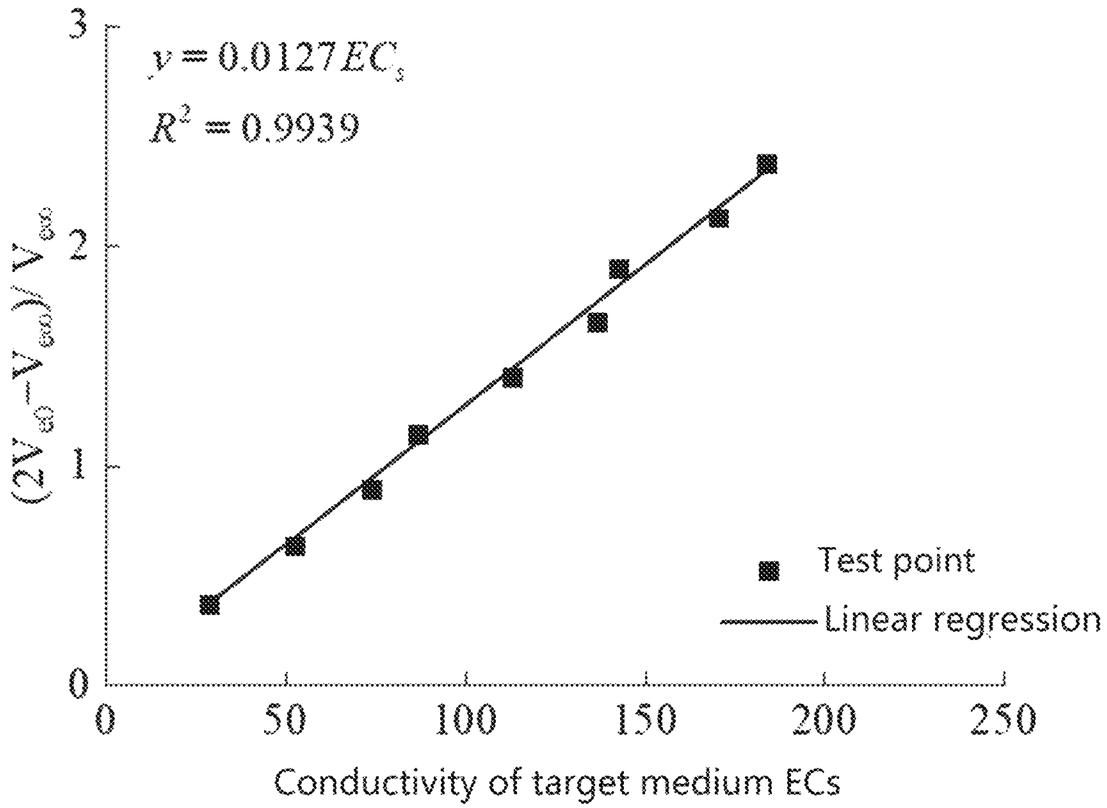
FIG. 3 is a analysis result map of the waveguide geometric dimensioning $C_e$ of the present invention.

S2, according to the electrical properties of the target medium, configuring NaCl solutions at concentrations of 0.003, 0.005, 0.007, 0.009, 0.011, 0.013, 0.015, 0.017, 0.019 mol/L, then testing respectively the time domain reflection waveform graphs of NaCl solutions by invasive and non-invasive time domain reflection probes at a constant temperature, finally, according to the time domain reflection waveform graphs tested by the invasive time domain reflection probes, calculating the conductivity of the solutions according to formula (9), and obtaining the initial voltage $V_{e0}$ of the electromagnetic pulse and the stable voltage $V_{e\infty}$ after multiple reflections from the time domain reflection waveform graphs tested by the non-invasive time domain reflection probes. Further, using the conductivity mixed model formula (10) and combining the expression formula of effective conductivity tested by the non-invasive time domain reflection probe, the conductivity and conductivity of circuit board substrate medium tested by the invasive time domain reflection probes, according to the conductivity mixed model, making the regression analysis on formula (12), finally, obtaining the waveguide geometric dimensioning $C_e$ (0.0127) of the non-invasive time domain reflection probes. Specifically, the analysis results of the waveguide geometric dimensioning $C_e$ of the non-invasive time domain reflection probes are shown in FIG. 3.

Example 1 Sandy Soil

Fujian standard sand with a maximum dry density of 1.638 g/cm$^3$, a minimum dry density of 1.349 g/cm$^3$ and a specific gravity of 2.67, $D_{10}$ is 0.11 mm, $D_{50}$ is 0.16 mm, $D_{60}$ is 0.175 mm.

Figure 4A:
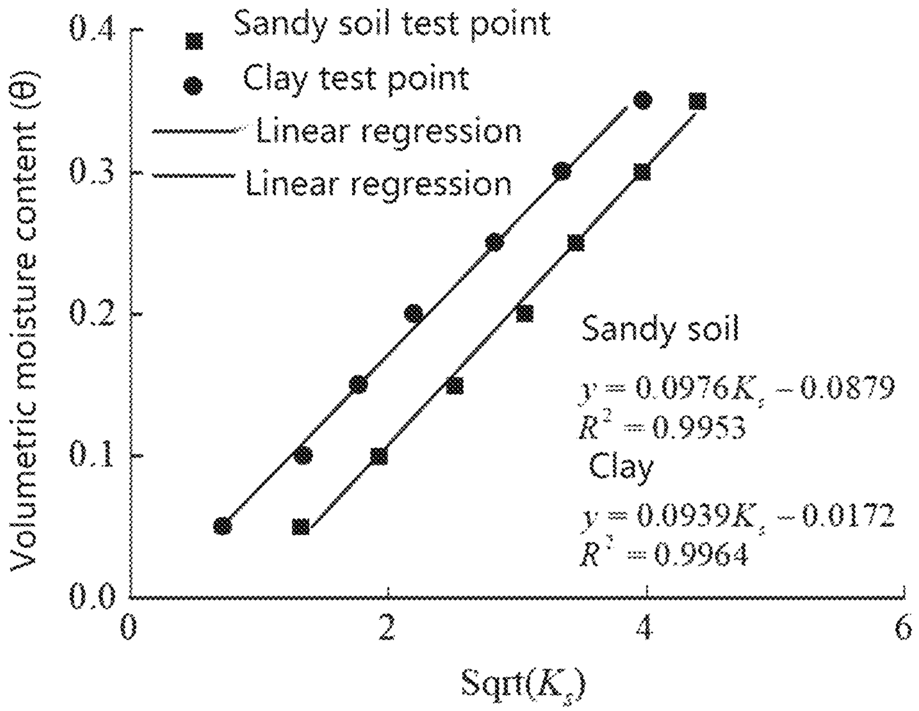
Figure 4B:
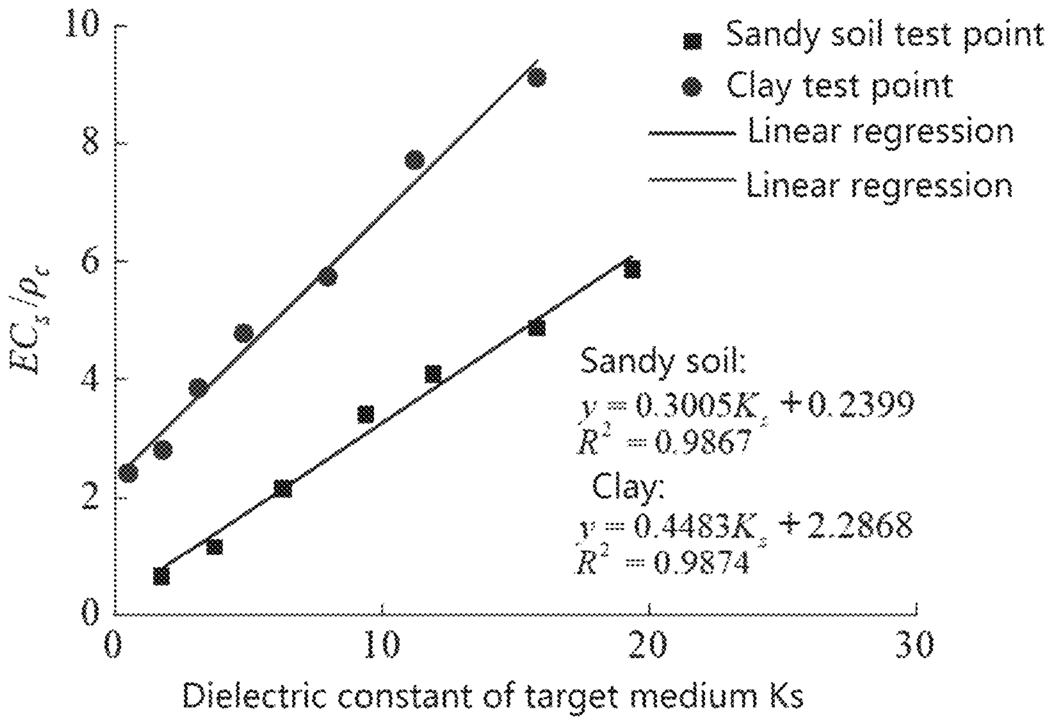

S3. by keeping the dry density of the soil constant and changing the moisture content, configuring the dried and sieved soil to compacted soil samples with volumetric moisture content of 5%, 10%, 15%, 20%, 25%, 30% and 35%, then combining with the waveguide length $L_e$ and geometric dimensioning $C_e$ of the non-invasive time domain reflection probes, adopting the time domain reflection waveform graphs of the compacted soil samples tested by non-invasive time domain reflection probes at a constant temperature and calculating the dielectric constant and conductivity of the soil according to formulas (15) and (16). Further, using the calculation formulas (17) and (18) to make regression analysis of dielectric constant and conductivity of the soil tested by formulas (15) and (16) with moisture content and density, then the values of the obtained calibration parameters $a_1$, $b_1$, $c_1$ and $d_1$ are 0.0976, −0.0879, 0.3005 and 0.2399 respectively. Specifically, the analysis results of the correlation parameters of the dielectric constant and conductivity of sandy soil calibrated by non-invasive time domain reflection probes with moisture content and density are shown in FIGS. 4A and 4B, respectively.

Example 2 Clay

Kaolin, its contents of clay particles, powder particles, and sand particles are 59.96%, 40.51%, and 0%, respectively, and the specific gravity is 2.65; in addition, the liquid limit and plasticity limit of the clay are 65.35% and 40.04%, respectively.

S4. by keeping the dry density of the soil constant to change the moisture content, configuring the dried and sieved soil to the compacted soil samples with volumetric moisture content of 5%, 10%, 15%, 20%, 25%, 30% and 35%, then combining with the waveguide length $L_e$ and geometric dimensioning $C_e$ of the non-invasive time domain reflection probes, adopting the time domain reflection waveform graphs of the compacted soil samples tested by non-invasive time domain reflection probes at a constant temperature and calculating the dielectric constant and conductivity of the soil according to formulas (15) and (16).

Further, using the calculation formulas (17) and (18) to make regression analysis of dielectric constant and conductivity of the soil tested by formulas (15) and (16) with moisture content and density, then the values of the obtained calibration parameters $a_1$, $b_1$, $c_1$ and $d_1$ are 0.0939, −0.0172, 0.4483 and 2.2868 respectively.

Specifically, the analysis results of the correlation parameters of the dielectric constant and conductivity of clay calibrated by non-invasive time domain reflection probes with moisture content and density are shown in FIGS. 4A and 4B, respectively.

In summary, the present invention of a non-invasive time domain reflection probe calibration method and system has the following characteristics:

(1) it has the advantages of clear theory, accurate calibration results, wide application range, reliable technology, convenient operation and strong practicability;

(2) it uses the difference of dielectric properties of different medium, it uses a dielectric mixed model to determine the sensitivity of the target medium tested by the non-invasive time domain reflection probes, and the physical meaning of this index is clear and determines the test accuracy of the probe;

(3) by using a dielectric/conductivity mixed model, it can realize the accurate calibration of the waveguide length and geometric dimensioning of the non-invasive time domain reflection probe, and improve the accuracy of the target medium's dielectric constant and conductivity tested by non-invasive time domain reflection probes;

(4) it can establish a link of the dielectric constant and electrical conductivity of compacted soil tested by non-invasive time domain reflection probes with density the volumetric moisture content of the soil, which provides a theoretical support for the laboratory test and engineering application of the probes in the field of geotechnical engineering; and (5) it extends the existing calibration method of time domain reflection probes, possesses a stronger practicability for the laboratory test and engineering application, and can become a new means in the field of calibration technology of geotechnical engineering measuring instruments.

Technical personnel in this field should understand that the examples of this application may be provided as a method, a system, or a computer program product. Therefore, this application may take the form of a full hardware embodiment, a full software embodiment, or a combination of software and hardware embodiments. Moreover, this application may take the form of a computer program product implemented on one or more mediums which contains computer available storage media (including but not limited to disk memory, CD-ROM, optical memory, etc.) with computer available program code.

This application is described by reference to the method, equipment (system) and flow chart of computer program products and/or block diagram according to the embodiments of this application. It should be understood that two different conditions can be realized by computer program instructions, wherein, one is each process and/or block in the flow chart and/or block diagram, the other is process and/or block diagram in the flowchart and/or block diagram. These computer program instructions can be provided to general purpose computers, special purpose computers, embedded processors or processors of other programmable data processing devices to produce a machine, which is a device that enables instructions executed by a computer or other programmable data processing device's processor to be used to implement functions specified in one or more of the flow charts and/or in one or more of the block diagrams.

These computer program instructions can also be stored in a computer-readable memory that can guide a computer or other programmable data processing equipment to work in a specific way, so that the instructions stored in the computer-readable memory produce a manufactured product including an instruction device, and the instruction device implements the functions specified a process or multiple processes in the flow chart and/or a block or multiple blocks of the block diagram.

These computer program instructions can also be loaded onto computers or other programmable data processing devices, so that a series of operation steps can be performed on computers or other programmable devices to generate computer-implemented processing, thereby instructions executed on a computer or other programmable device provide steps for implementing functions specified a process or multiple processes in the flow chart and/or a block or multiple blocks of the block diagram.

The above content only explains the technical idea of the invention, and cannot limit the scope of protection of the invention, any change made on the basis of the technical scheme according to the technical idea proposed by the invention falls within the scope of protection of the claim of the invention.

What is claimed is:

1. A non-invasive time domain reflection probe calibration method, comprising:

s1: using different volume radio of ethanol and deionized water mixed solution to calculate a test target's medium weight coefficient and waveguide length of non-invasive time domain reflection probes; wherein s1 comprises:

s101: mixing ethanol and deionized water to form at least 4 groups of mixed solution with different concentrations, then using invasive time domain reflection probes and the non-invasive time domain reflection probes to test respectively time domain reflection waveform graphs of mixed solutions with different concentrations, finally calculating a dielectric constant of the mixed solutions according to the time domain reflection waveform graphs of invasive time domain reflection probes test, and obtaining a propagation time of electromagnetic wave along the waveguide $\Delta t_e$ from the time domain reflection waveform graphs tested by the invasive time domain reflection probes; and s102: according to a dielectric mixed model, a regression analysis is used to study an effective dielectric constant tested by the non-invasive time domain reflection probes, the dielectric constant of mixed solution tested by the invasive time domain reflection probes test and a dielectric constant tested by circuit board substrate medium, calculating and obtaining a test target's medium weight coefficient and a waveguide length tested by the non-invasive time domain reflection probes;

wherein the test target's medium weight coefficient m and waveguide length Le of the non-invasive time domain reflection probes are:

$$m = \frac{a}{4L_e^2}$$

$$L_e = \sqrt{\frac{aK_m + b}{4K_m}}$$

wherein, $K_m$ is the dielectric constant of circuit board substrate medium, a and b are fitting parameters of dielectric mixed model regression analysis formula;

s2: based on the test target's medium weight coefficient, using different concentrations of NaCl solution to calibrate a waveguide geometric dimensioning of the non-invasive time domain reflection probes; wherein s2 comprises:

s201: considering a conductivity gradient and configuring more than or equal to four groups of different concentrations of NaCl solutions, then using invasive time domain reflection probes and the non-invasive time domain reflection probes to test time domain reflection waveform graphs of NaCl solutions at a constant temperature, calculating a conductivity of NaCl solution according to the time domain reflection waveform graphs tested by the invasive time domain reflection probes, and obtaining an initial voltage of an electromagnetic pulse $V_{e0}$ and a stable voltage after multiple reflections $V_{e\infty}$ from time domain reflection waveform graphs tested by the non-invasive time domain reflection probes;

wherein the conductivity of NaCl solution tested by the invasive time domain reflection probes is:

$$EC_s = \frac{1}{C}\left(\frac{2V_0 - V_\infty}{V_\infty}\right)$$

wherein, C is the waveguide geometric dimensioning of the invasive time domain reflection probes, and $V_0$ is the initial voltage of the electromagnetic pulse tested by the invasive time domain reflection probes, and $V_\infty$ is the stable voltage after multiple reflections tested by the invasive time domain reflection probes; and s202: according to a conductivity mixed model, using a regression analysis to study an effective conductivity tested by the non-invasive time domain reflection probes, a conductivity tested by the invasive time domain reflection probes and a conductivity of circuit board substrate medium, calculating and obtaining a waveguide geometric dimensioning $C_g$ of the non-invasive time domain reflection probes;

wherein the waveguide geometric dimensioning $C_g$ of the non-invasive time domain reflection probes is:

$$C_e = \frac{2V_{e0} - V_{e\infty}}{V_{e\infty}EC_s}$$

wherein, $EC_s$ is the conductivity of NaCl solution tested by the invasive time domain reflection probes; and s3: preparing compacted soil samples with known different moisture contents and densities, according to the waveguide length and waveguide geometric dimensioning of the non-invasive time domain reflection probes, calibrating a correlation parameter of compacted soil samples' dielectric constant and conductivity with moisture content and density; wherein s3 comprises:

s301: configuring dried and sieved soil as compacted soil samples covering a range of tested moisture content, and a number of compacted soil samples is greater than or equal to 4 groups, then combining with the waveguide length and waveguide geometric dimensioning of the non-invasive time domain reflection probes, using the non-invasive time domain reflection probes to test the time domain reflection waveform graphs of the compacted soil samples, and using a dielectric and conductivity mixed model to calculate a dielectric constant $K_s$ and a conductivity EC, of the compacted soil samples respectively; and wherein the dielectric constant $K_s$ and the conductivity $EC_s$ of the compacted soil samples are respectively:

$$K_s = \frac{K_e + (m-1)K_m}{m}$$

$$EC_s = \frac{2V_{e0} - V_{e\infty}}{C_e V_{e\infty}}$$

wherein, $K_e$ is an effective dielectric constant tested by the non-invasive time domain reflection probes, m is a test target's medium weight coefficient of the non-invasive time domain reflection probes, $K_m$ is a dielectric constant of the circuit board substrate medium, $V_{e0}$ is an initial voltage of the electromagnetic pulse tested by the non-invasive time domain reflection probes, $V_{e\infty}$ is a stable voltage after multiple reflections tested by the non-invasive time domain reflection probes, and $C_e$ is a waveguide geometric dimensioning of the non-invasive time domain reflection probes; and s302: using formula to make a regression analysis of the dielectric constant $K_s$ and the conductivity EC of the soil obtained by the dielectric and conductivity mixed model, and obtaining calibration parameters $a_1$, $b_1$, $c_1$ and $d_1$;

wherein a volumetric moisture content θ and a soil density $\rho_e$ of the compacted soil samples are calculated as follows:

$$\theta = a_1\sqrt{K_s} + b_1$$

$$\frac{EC_s}{\rho_c} = c_1 K_s + d_1.$$

2. A non-invasive time domain reflection probe calibration system, which is used for implementing the non-invasive time domain reflection probe calibration method according to claim 1, comprising:

a calibration module, wherein the calculation module is used to calculate test target's medium weight coefficient and waveguide length of non-invasive time domain reflection probes by using mixed solutions of ethanol and deionized water with different volume ratios;

a regression module, wherein the regression module is used to utilize test target's medium weight coefficient obtained by the calculation module, and use different concentrations of NaCl solution to calibrate a waveguide geometric dimensioning of the non-invasive time domain reflection probes;

a calibration module, wherein the calibration module is used to prepare compacted soil samples with known different moisture contents and densities, according to the waveguide length of the non-invasive time domain reflection probes obtained by the calibration module and waveguide geometric dimensioning obtained by the regression module, calibrating correlation parameters of compacted soil samples' soil dielectric constant and conductivity with moisture content and density.

* * * * *